US00PP29756P3

(12) United States Plant Patent
van Langen

(10) Patent No.: US PP29,756 P3
(45) Date of Patent: Oct. 16, 2018

(54) ***ECHEVERIA* PLANT NAMED 'AMIECH1606'**

(50) Latin Name: *Echeveria agavoides*
Varietal Denomination: AMIECH1606

(71) Applicant: NovoAmi B.V., Heerhugowaard (NL)

(72) Inventor: Gerard van Langen, Heerhugowaard (NL)

(73) Assignee: NovoAmi B.V., Heerhugowaard (NL)

( * ) Notice: Subject to any disclaimer, the term of this patent is extended or adjusted under 35 U.S.C. 154(b) by 41 days.

(21) Appl. No.: 15/530,334

(22) Filed: Dec. 23, 2016

(65) Prior Publication Data

US 2018/0184566 P1 Jun. 28, 2018

(51) Int. Cl.
*A01H 5/12* (2018.01)

(52) U.S. Cl.
USPC ..... Plt./373
CPC ..... *A01H 5/12* (2013.01)

(58) Field of Classification Search
USPC ..... Plt./373
See application file for complete search history.

*Primary Examiner* — Susan McCormick Ewoldt
*Assistant Examiner* — Karen M Redden
(74) *Attorney, Agent, or Firm* — Samuel R. McCoy, Jr.

(57) ABSTRACT

A new and distinct *Echeveria agavoides* cultivar named 'AMIECH1606' which is characterized by a flattened globular plant shape, foliage arranged in a compact rosette, broad ovate foliage with a short apiculate apex, yellow-green juvenile foliage emerging from the center of the rosette which is suffused with greyed-purple towards the apex, foliage which becomes progressively suffused with greyed-purple with age and exposure to ultraviolet light and with margins becoming vivid red, mature foliage at the outermost whorls of the rosette which is generally colored greyed-purple, suffused with grey towards the apex and margined vivid red, as well as the stability of these characteristics from generation to generation.

4 Drawing Sheets

Latin name of the genus and species: The Latin name of the genus and species of the novel variety disclosed herein is *Echeveria agavoides.*

Variety denomination: The inventive variety of *Echeveria* disclosed herein has been given the variety denomination 'AMIECH1606'.

BACKGROUND OF THE INVENTION

Parentage: 'AMIECH1606' is a seedling selection resulting from the self-pollination of the species, *Echeveria agavoides* (unnamed and unpatented). The self-pollination event occurred in the autumn of 2011 at a commercial greenhouse in Heerhugowaard, the Netherlands. Seed was harvested by the inventor, then germinated, and the resulting seedlings were then grown to a mature size. In summer of 2013, one seedling was observed to exhibit unique foliage characteristics and growth habit. The seedling was isolated for further evaluation in order to confirm the distinctness and stability of the characteristics first observed. Upon confirmation of distinctness and stability, 'AMIECH1606' was selected for commercialization in the autumn of 2014.

Asexual Reproduction: Asexual reproduction of the new cultivar 'AMIECH1606', by way of rooting leaf cuttings, was first initiated in the summer of 2015 at the inventor's commercial greenhouse in Heerhugowaard, the Netherlands. Through five subsequent generations, the unique features of this cultivar have proven to be stable and true to type.

SUMMARY OF THE INVENTION

The cultivar 'AMIECH1606' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'AMIECH1606'. These characteristics in combination distinguish 'AMIECH1606' as a new and distinct *Echeveria agavoides* cultivar:

1. 'AMIECH1606' exhibits foliage arranged in a compact rosette; and
2. 'AMIECH1606' exhibits broad ovate foliage with a short apiculate apex; and
3. 'AMIECH1606' exhibits yellow green juvenile foliage emerging from the center of the rosette, which is suffused with greyed-purple towards the apex; and
4. 'AMIECH1606' exhibits foliage which becomes progressively suffused with greyed-purple with age and exposure to ultraviolet light, margins becoming vivid red, moving outward from the center of the rosette; and
5. 'AMIECH1606' exhibits mature foliage at the outermost whorls of the rosette which is generally colored greyed-purple, suffused with grey towards the apex, and margined vivid red.

BOTANICAL DESCRIPTION OF THE PLANT

Figure 1:
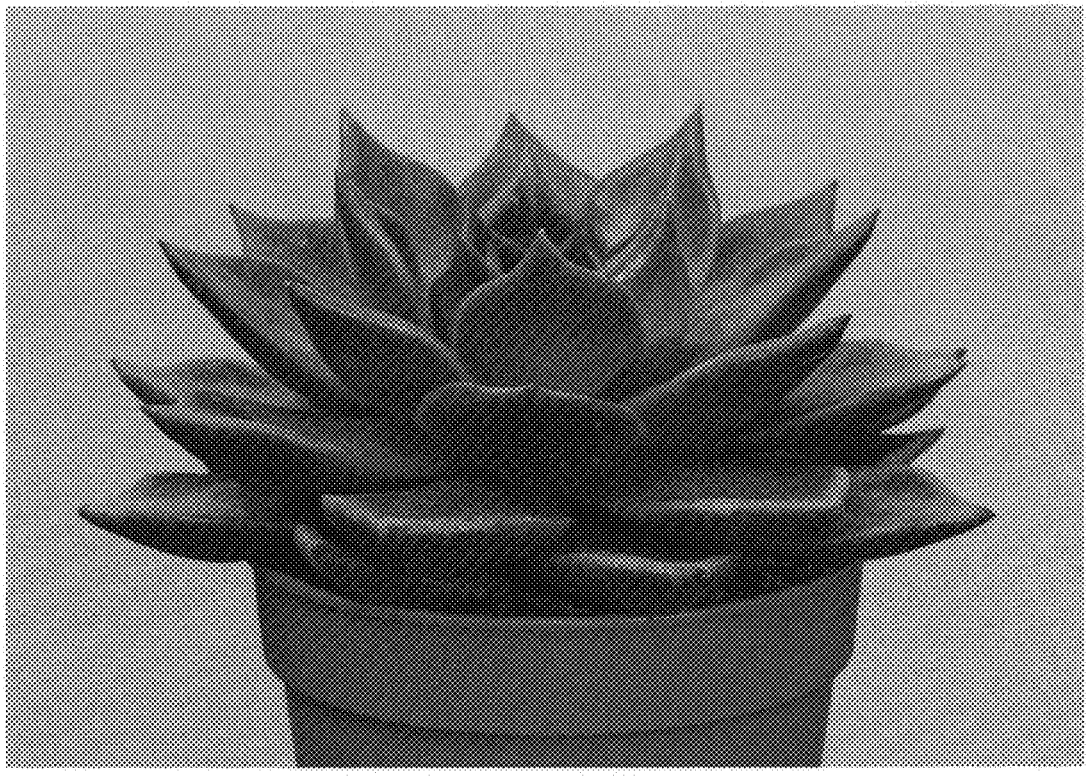
FIG. 1 illustrates, as nearly true as it is reasonably possible to make the same in color photographs of this type, an exemplary plant of 'AMIECH1606' grown in a commercial greenhouse in Heerhugowaard, the Netherlands. This plant is approximately 9 months old, shown planted in an 11 cm container.
Figure 2:
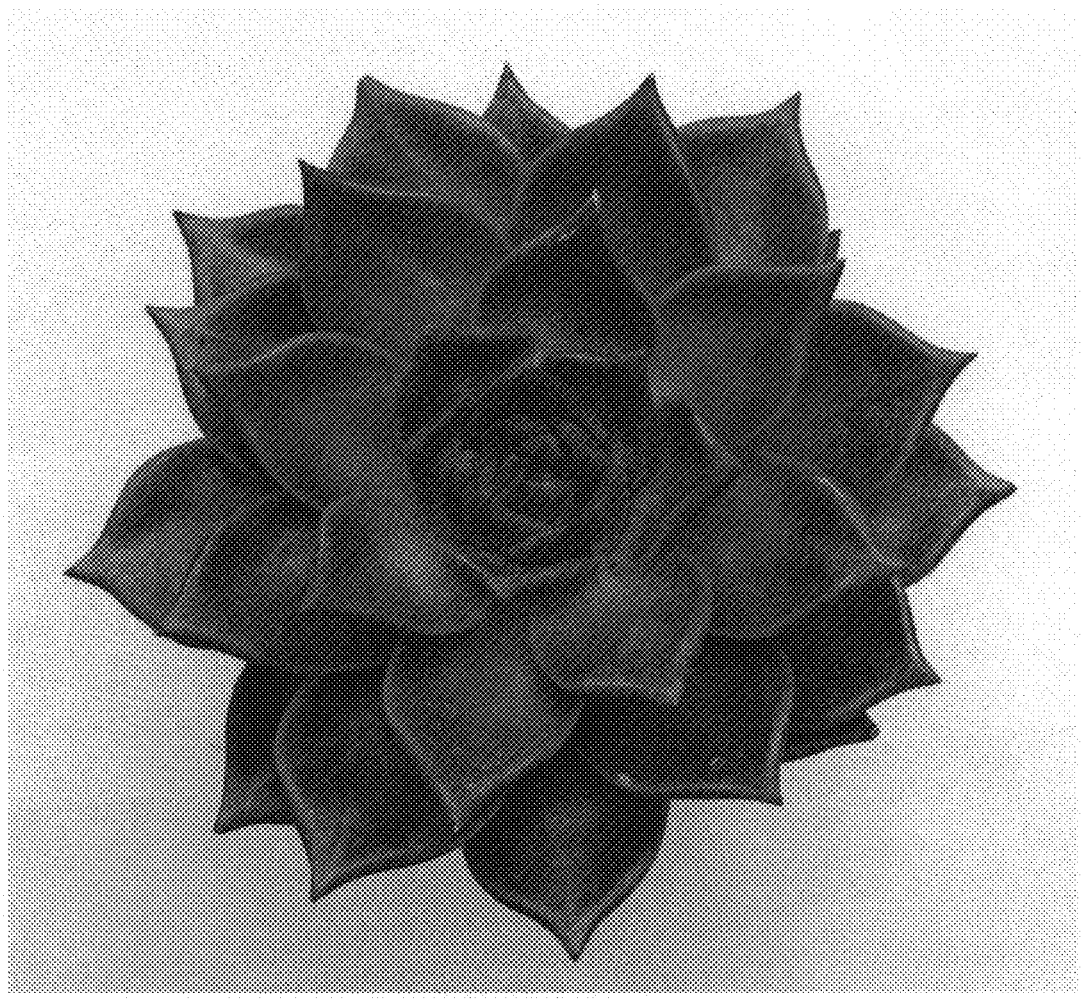
FIG. 2 illustrates, as nearly true as it is reasonably possible to make the same in color photographs of this type, the typical foliage arrangement of 'AMIECH1606'.
Figure 3:
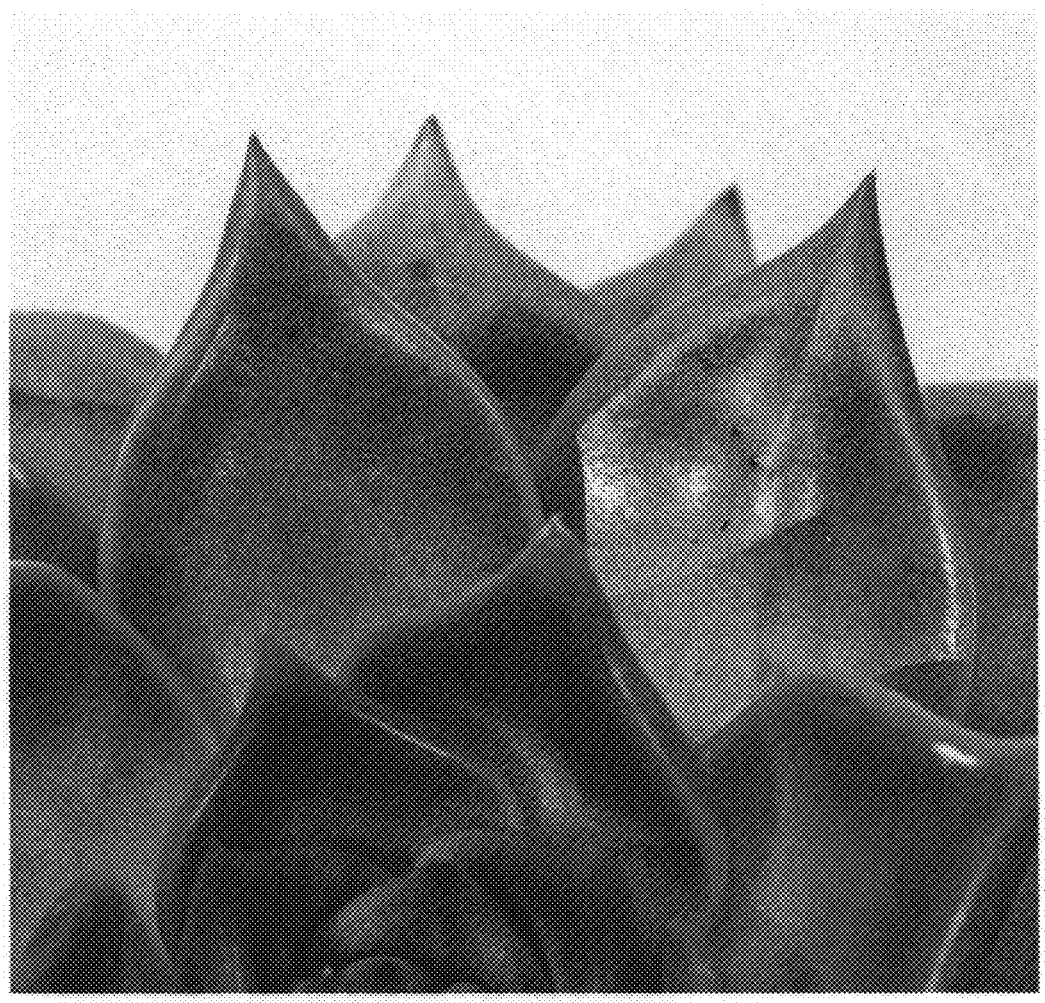
FIG. 3 illustrates, as nearly true as it is reasonably possible to make the same in color photographs of this type, the foliage color from the center of the rosette (juvenile foliage) to the outer most whorl of the rosette (mature foliage) of 'AMIECH1606'.
Figure 4:
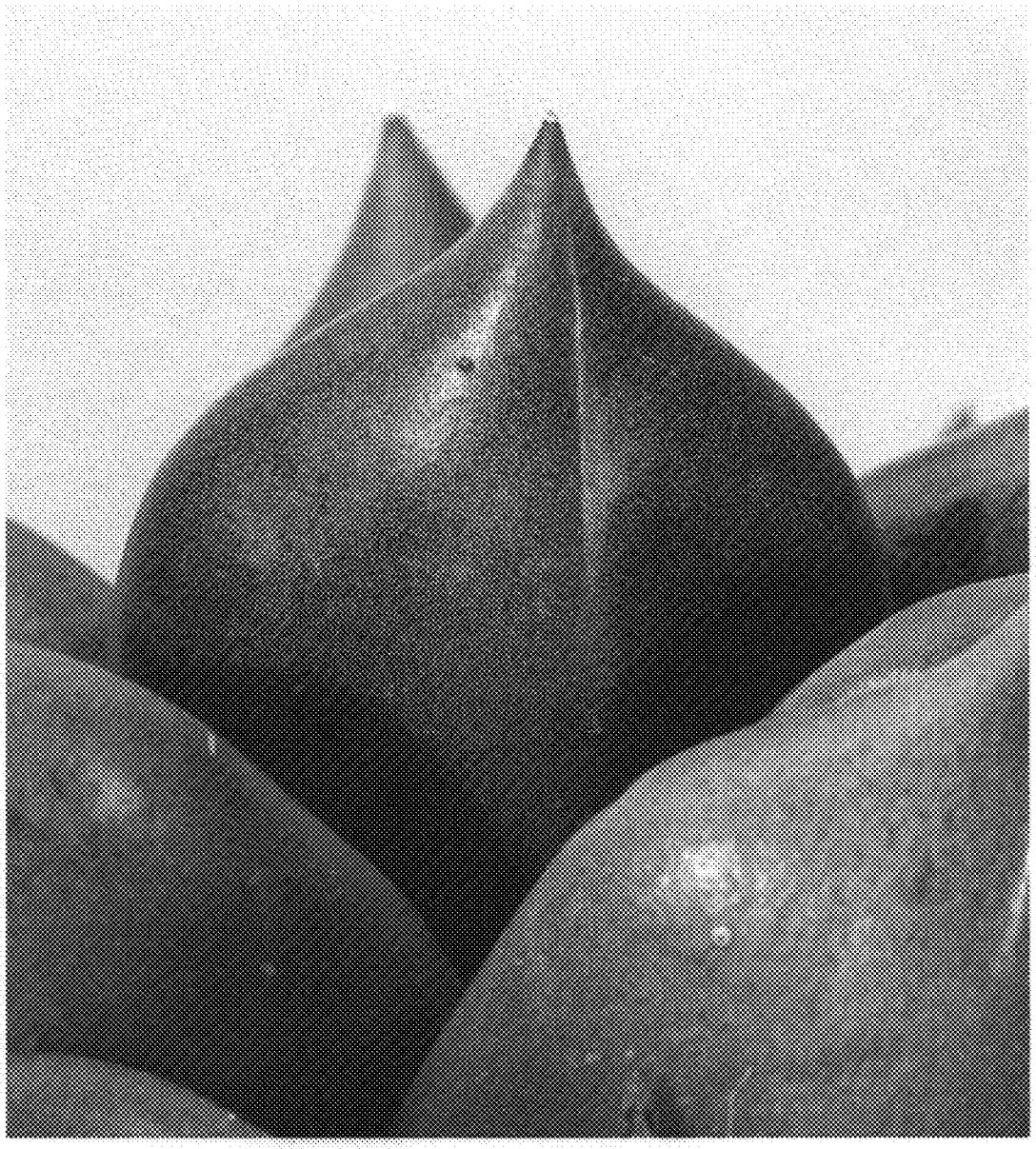
FIG. 4 illustrates, as nearly true as it is reasonably possible to make the same in color photographs of this type, the abaxial surface of the mature foliage 'AMIECH1606'.

The following observations and measurements made in October of 2016 describe averages from a sample set of six specimens of 9 months old 'AMIECH1606' plants grown in 11 cm nursery containers at commercial greenhouse in Heerhugowaard, the Netherlands. Plants were produced using conventional greenhouse production protocols for *Echeveria* which consisted of minimal irrigation and fertilizer applications, and chemical pest and disease control measures against mealy bug and Botrytis as required. Plants were grown under approximately 50 percent shade after propagation and later exposed to full sun once they began to mature. No photoperiodic treatments or artificial light was given to the plants.

Those skilled in the art will appreciate that certain characteristics will vary with older or, conversely, with younger plants. 'AMIECH1606' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climatic and cultural conditions. Color notations are based on *The Royal Horticultural Society Colour Chart*, The Royal Horticultural Society, London, 2015 (sixth edition).

A botanical description of 'AMIECH1606' and a comparison with the parent and closest known comparator, *Echeveria agavoides*, is provided below.

Plant description:

*Growth habit*.—Succulent perennial with foliage growing in a non-branched basal rosette.

*Plant shape*.—Flattened globular.

*Height from soil level to top of foliar plane*.—8.0 cm.

*Plant spread*.—Average of 18.1 cm.

*Growth rate*.—Moderate.

*Plant vigor*.—Moderate.

*Propagation*.—Type — Leaf cuttings. Time to initiate rooting — Approximately 21 to 35 days at 18 degrees Celsius. Crop time — Approximately 18 to 22 weeks to produce a marketable plant in an 11 cm container.

*Disease and pest resistance or susceptibility*.—Neither resistance nor susceptibility to typical *Echeveria agavoides* pests and diseases has been observed.

*Environmental tolerances*.—Adapt to, at least, USDA Zones 10 to 12 and temperatures as high as 40 degrees Celsius; moderate tolerance to rain yet drought tolerant once established; high tolerance to wind.

Root system:

*General*.—Fine, well-branched fibrous roots.

Stems:

*Branching habit*.—Leaves in a non-branching basal rosettes; no main branches or lateral branches present.

Foliage:

*Arrangement*.—Rosette.

*Division*.—Simple.

*Attachment*.—Sessile.

*Quantity*.—Approximately 42 leaves per rosette.

*Shape*.—Thick, succulent leaves which are obovate to near oblong.

*Dimensions*.—7.5 cm long, 4.2 cm wide, and 1.3 cm thick, on average.

*Aspect*.—Flat to slightly concave and carinate.

*Apex*.—Short apiculate.

*Base*.—Broad cuneate.

*Margin*.—Entire; not undulated or lobed.

*Pubescence, texture and luster of the adaxial surface*.—Glabrous, smooth, and moderately glossy; lightly to moderately pruinose.

*Pubescence, texture and luster of the abaxial surface*.—Glabrous, smooth, and moderately glossy; lightly to moderately pruinose.

*Color*.—Juvenile foliage, adaxial surface — Yellow-green, in between RHS N148C and N148D; margins and distal portion of the leaf surface towards the apex are in between greyed-orange, nearest to RHS 177A, and greyed-red, nearest to RHS 178A; apex is greyed-purple, RHS 183B. Juvenile foliage, abaxial surface — Greyed-green, in between RHS 193A and 193B; distal portion of the leaf surface towards the apex is greyed-orange, in between RHS 176B and 177A, yet slightly darker; apex is greyed-purple, RHS 183B. Mature foliage, adaxial surface — Greyed-orange, nearest to RHS N176B, and suffused with grey towards the apex, nearest to RHS 201A; base is yellow-green, in between RHS 145D and 150D; margined greyed-red, in between RHS 181B and 181C. Mature foliage, abaxial surface — Greyed-red, nearest to RHS 182B, and suffused with grey towards the apex, nearest to RHS 201A; base is yellow-green, in between RHS 145C and 145D; margined greyed-red, in between RHS 181B and 181C.

*Venation*.—No venation is visible.

*Petiole*.—No petiole; leaves are sessile.

Inflorescence: No flowering has been observed to date.

Comparisons with the parent plant and closest known comparator: Plants of the new cultivar 'AMIECH1606' differ from the parent, *Echeveria agavoides*, which is also the closest known comparator, in the following characteristics described in Table 1 below.

TABLE 1

| Characteristic | 'AMIECH1606' | *Echeveria agavoides* |
|---|---|---|
| Leaf thickness. | Thicker then the parent. | Thinner than 'AMIECH1606'. |
| Leaf apex. | Short apiculate. | Acute. |
| Leaf width. | Wider than the parent. | Narrower than 'AMIECH1606'. |
| General coloration of mature foliage. | Greyed-purple and suffused with grey towards the apex; margined vivid red | Yellow-green and suffused with greyed-purple towards the apex and margins. |

Plants of the new cultivar 'AMIECH1606' differ from the commercial variety, *Echeveria agavoides* 'Dark Moon' (U.S. Plant Pat. No. 28,685), in the following characteristics described in Table 2 below.

TABLE 2

| Characteristic | 'AMIECH1606' | 'Dark Moon' |
|---|---|---|
| Plant size. | Smaller than 'Dark Moon'. | Larger than 'AMIECH1606'. |
| Foliage attitude. | More relaxed than 'Dark Moon'. | More erect than 'AMIECH1616'. |

TABLE 2-continued

| Characteristic | 'AMIECH1606' | 'Dark Moon' |
|---|---|---|
| General coloration of mature foliage. | Greyed-purple and suffused with grey towards the apex; margined vivid red. | Dark violet black. |

That which is claimed is:

1. A new and distinct variety of *Echeveria agavoides* plant named 'AMIECH1606', substantially as described and illustrated herein.

* * * * *